US009226709B2

(12) United States Patent
Montague

(10) Patent No.: US 9,226,709 B2
(45) Date of Patent: Jan. 5, 2016

(54) ICE MESSAGE SYSTEM AND METHOD

(71) Applicant: Medtronic MiniMed, Inc., Northridge, CA (US)

(72) Inventor: George J. Montague, Minneapolis, MN (US)

(73) Assignee: Medtronic MiniMed, Inc., Northridge, CA (US)

( * ) Notice: Subject to any disclaimer, the term of this patent is extended or adjusted under 35 U.S.C. 154(b) by 79 days.

(21) Appl. No.: 14/071,261

(22) Filed: Nov. 4, 2013

(65) Prior Publication Data

US 2015/0123800 A1 May 7, 2015

(51) Int. Cl.
*G08B 23/00* (2006.01)
*A61B 5/00* (2006.01)

(52) U.S. Cl.
CPC ............. *A61B 5/6801* (2013.01); *A61B 5/0022* (2013.01); *A61B 5/7282* (2013.01)

(58) Field of Classification Search
CPC .. G08B 21/0453; G08B 21/12; G08B 25/012; G08B 31/00; H04L 67/12; H04L 63/08; H04L 67/18; H04L 67/306; B60Q 1/00; B60R 16/037; B60R 16/0373; B60R 25/00; B60W 40/09; B60W 50/08; G01C 21/00
USPC ............ 340/573.1, 870.16, 7.51, 7.55, 572.8; 604/503, 66, 890.1, 504; 600/549, 300, 600/301
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,398,727 B1 * | 6/2002 | Bui et al. ..................... 600/300 |
| 6,544,212 B2 | 4/2003 | Galley et al. |
| 6,558,351 B1 | 5/2003 | Steil et al. |
| 6,591,876 B2 | 7/2003 | Safabash |
| 6,616,606 B1 * | 9/2003 | Petersen et al. ............... 600/300 |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |

(Continued)

*Primary Examiner* — Daniel Previl
(74) *Attorney, Agent, or Firm* — Medtronic MiniMed, Inc.

(57) ABSTRACT

An ICE message system and method having a medical system for use with a patient, the medical system including a personal medical device attached to the patient and a display operably connected to the personal medical device. The personal medical device includes a monitor operable to detect an emergency condition at the personal medical device, and a processor operably connected to the monitor and operable to select an ICE message in response to the emergency condition. The display is operable to display the ICE message, which includes emergency contact information.

20 Claims, 7 Drawing Sheets

(56) References Cited

U.S. PATENT DOCUMENTS

| | | |
|---|---|---|
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 * | 6/2010 | Talbot et al. ............. 600/365 |
| 7,785,313 B2 * | 8/2010 | Mastrototaro ............. 604/503 |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2002/0013538 A1 * | 1/2002 | Teller ............. 600/549 |
| 2005/0049514 A1 * | 3/2005 | Iwamiya et al. ............. 600/503 |
| 2007/0123819 A1 | 5/2007 | Mernoe et al. |
| 2007/0241261 A1 * | 10/2007 | Wendt ............. 250/221 |
| 2010/0160861 A1 * | 6/2010 | Causey et al. ............. 604/131 |

* cited by examiner

ICE MESSAGE SYSTEM AND METHOD

TECHNICAL FIELD

The technical field of this disclosure is personal medical systems, particularly, ICE message systems and methods.

BACKGROUND OF THE INVENTION

Advances in electronics have resulted in the miniaturization of medical devices such that medical devices which previously required large stationary equipment can now be worn about the person, who can be monitored or receive treatment while pursuing normal daily tasks.

One area of such advances has been in the treatment of diabetes. An estimated twenty-six million people in the United States, or about 8% of the population, have diabetes. This percentage is expected to increase in the near-term as the population ages. Wearable glucose monitors and insulin pumps have been developed which allow persons under treatment for diabetes to be monitored and receive insulin while carrying on their day-to-day tasks.

Even with improved treatment, emergencies can arise. Patients can have unusual reactions to medication or equipment can malfunction. Unfortunately, the patient may not notice a malfunction, or may be incapacitated and unable to respond to the emergency. Bystanders or emergency personnel on site may lack information about the patient, making emergency treatment risky and ineffective. In addition, the patient may not have personal identification or contact information for doctors or relatives from whom vital medical information could be obtained.

It would be desirable to have an ICE message and system that would overcome the above disadvantages.

SUMMARY OF THE INVENTION

One aspect of the invention provides a medical system for use with a patient, the medical system including a personal medical device attached to the patient and a display operably connected to the personal medical device. The personal medical device includes a monitor operable to detect an emergency condition at the personal medical device, and a processor operably connected to the monitor and operable to select an ICE message in response to the emergency condition. The display is operable to display the ICE message, which includes emergency contact information.

Another aspect of the invention provides a personal medical device attachable to a patient and operably connectable to a display, the personal medical device including a monitor operable to detect an emergency condition at the patient; and a processor operably connected to the monitor and being operable to select an ICE message in response to the emergency condition, the ICE message including emergency contact information presentable on the display.

Another aspect of the invention provides a method of emergency notification with a personal medical device attached to a patient, the method including detecting an emergency condition at the personal medical device attached to the patient; selecting an ICE message in response to the detected emergency condition; and displaying the ICE message.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION

Figure 1:
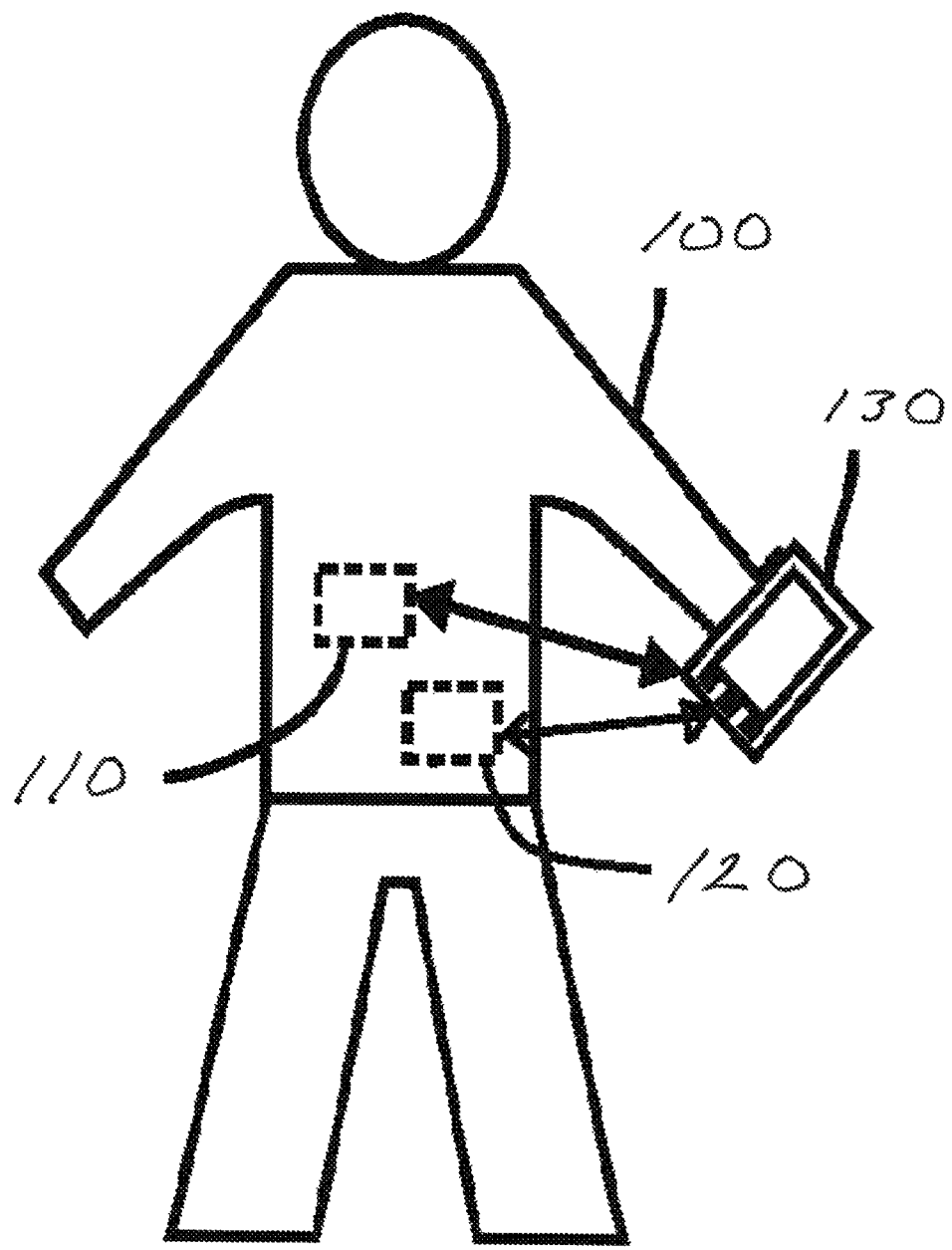
FIG. 1 is a schematic diagram of personal medical devices made in accordance with the invention.

FIG. 1 is a schematic diagram of personal medical devices made in accordance with the invention. In this example, the patient 100 and is wearing two personal medical devices, a therapy administration device 110 and a physiological monitoring device 120, both of which are in wired and/or wireless communication with an optional communication device 130 such as a relay device. In one embodiment, the therapy administration device 110 and the physiological monitoring device 120 can be combined as a single device. The personal medical device can be any personal medical device which delivers therapy to a patient and/or monitors a physiological parameter of the patient, as desired for a particular application. Exemplary personal medical devices include pumps, cell pumps, continuous glucose monitors, heart-rate monitors, ECG monitors, pulse oximeters, blood pressure monitors, respiration rate monitors, skin temperature monitors, electroencephalography (EEG) monitors, activity level monitors, vital sign monitors, and the like. In one embodiment, the therapy administration device 110 is an insulin delivery device and the physiological monitoring device 120 is a continuous glucose monitoring (CGM) device. In another embodiment, the personal medical device is a paired insulin delivery and CGM device. The personal medical device as defined herein can be any medical device designed to be carried or worn by a patient.

Figure 2:
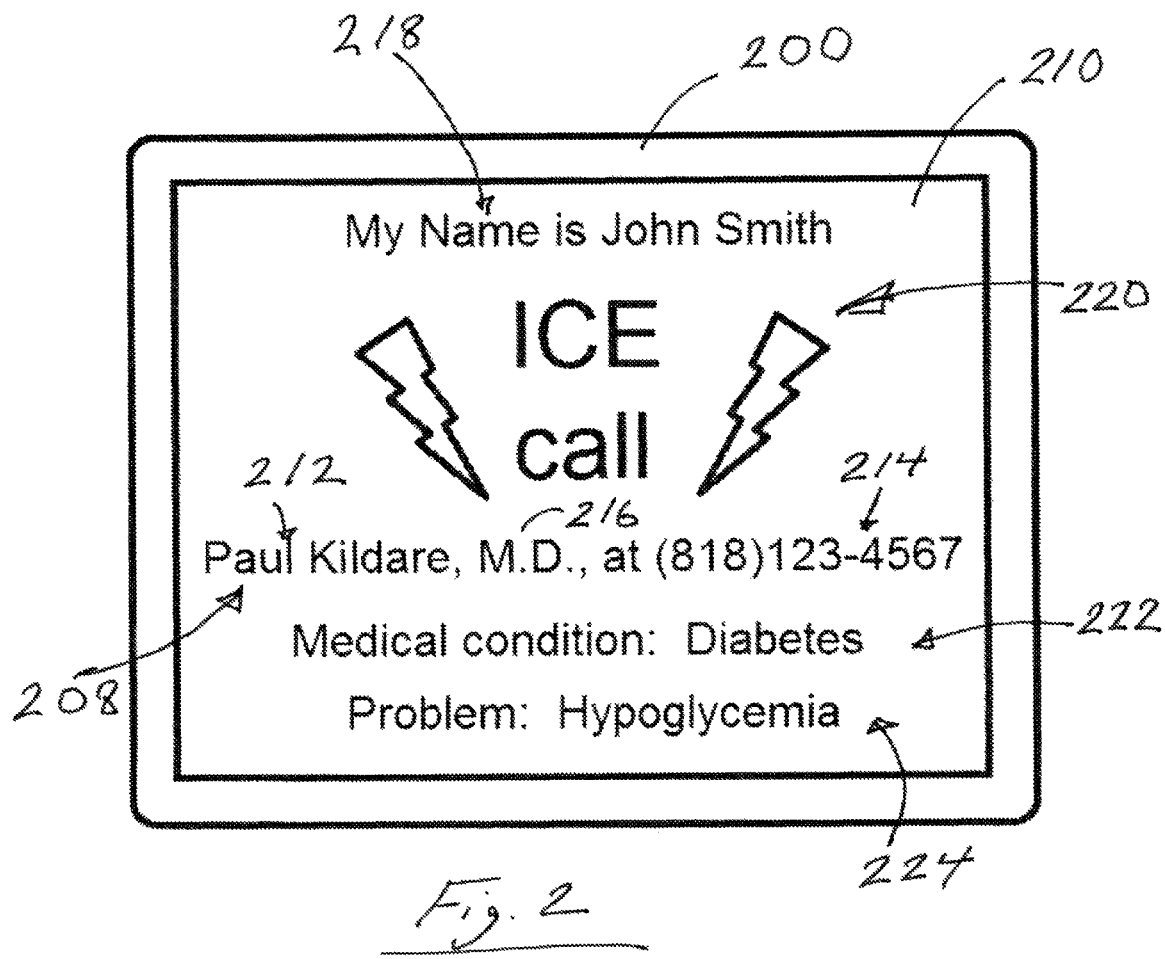
FIG. 2 is a schematic diagram of an ICE (In Case Of Emergency) message on a display of a personal medical system made in accordance with the invention.

FIG. 2 is a schematic diagram of an ICE (In Case Of Emergency) message on a display of a personal medical system made in accordance with the invention. The display is operably connected to a personal medical device and operable to display the ICE message, the ICE message including emergency contact information. The ICE message as defined herein can be any information that the patient desires to be displayed in case of an emergency, and includes emergency contact information.

The ICE message 210 is displayed on the display 200 and includes emergency contact information 208. In this example, the emergency contact information 208 includes contact name 212, telephone number 214, and relationship information 216. The ICE message 210 can also include a patient identifier 218, an ICE notice flag 220, a patient disease/condition identifier 222, and a prospective cause indication 224.

The emergency contact information 208 includes enough information that a person reading the ICE message 210 can contact the emergency contact. Exemplary information includes the name of the emergency contact and a communication address, such as a telephone number, an e-mail address, a social network (Facebook, Twitter) address, or the like. The emergency contact information 208 can also include relationship information to indicate the relationship between the patient and the emergency contact, such as physician, relative, spouse, work supervisor, school principal, or the like.

The ICE message 210 can also include other information to assist the person reading the ICE message 210. A patient identifier 218 can provide the name or number of a patient to be supplied to the emergency contact. An ICE notice flag 220 can draw attention to the display 200 in an emergency. In one embodiment, the ICE notice flag 220 can be animated. A patient disease/condition identifier 222 can alert the person reading the ICE message 210 to existing diseases or conditions of the patient which may be a factor in the emergency. In one example, the patient disease/condition identifier 222 can point out that the patient is diabetic.

A prospective cause indication 224 can provide a prospective cause of the emergency condition as determined by the processor of the personal medical device. If desired, the prospective cause indication 224 can be dynamic, changing as the monitor detects changes in the emergency condition and provides updated information to the processor. In one example, the monitor of the personal medical device is a continuous glucose monitoring (CGM) device. When the CGM device detects an emergency condition of low sugar, the processor can determine the prospective cause as low sugar and the prospective cause indication 224 can display a message such as hypoglycemia, low blood sugar, low glucose, or the like. When the CGM device detects an emergency condition of high sugar, the processor can determine the prospective cause as high sugar and the prospective cause indication 224 can display a message such as hyperglycemia, high blood sugar, high glucose, or the like. In another example, the monitor of the personal medical device is an equipment monitor the checks operation of the personal medical device. When the equipment monitor detects an emergency condition of pump failure, the processor can determine the prospective cause as pump failure and the prospective cause indication 224 can display a message such as pump failure, equipment failure, or the like. When the equipment monitor detects an emergency condition of low battery voltage, the processor can determine the prospective cause as battery failure and the prospective cause indication 224 can display a message such as battery failure, battery low, low voltage, or the like.

Referring generally to the personal medical systems of FIGS. 3-6, the personal medical systems include a personal medical device attached to a patient and a display operably connected to the personal medical device. The personal medical device includes a monitor operable to detect an emergency condition at the personal medical device, and a processor operably connected to the monitor and operable to select an ICE message in response to the emergency condition. The display is operable to display the ICE message, which includes emergency contact information.

The personal medical device can be any medical device designed to be carried or worn by a patient, and can be any personal medical device which delivers therapy to a patient and/or monitors a physiological parameter of the patient, as desired for a particular application. Exemplary personal medical devices include pumps, cell pumps, continuous glucose monitors, and the like.

The monitor of the personal medical device is operable to detect an emergency condition, such as a patient medical emergency or an equipment failure on the personal medical device. When the personal medical device is a continuous glucose monitoring (CGM) device monitoring blood sugar level, exemplary patient medical emergencies include hypoglycemia and hyperglycemia. When the personal medical device is an insulin delivery device, exemplary equipment failures include pump failure, battery failure, battery low, low battery voltage, or the like. In one example, the emergency condition is a medical emergency. In another example, the emergency condition is a failure to respond to a personal medical device alarm. In another example, the emergency condition is an equipment failure. In another example, the emergency condition is a failure to detect change in device position, when the personal medical device includes a location detector (GPS or cell location, for example) used to detect device position.

The processor of the personal medical device is operable to select an ICE message in response to an emergency condition received from the monitor. Exemplary processors include a central processing unit and a microprocessor. The processor can include or be attached to auxiliary equipment, such as memory, data storage, additional processors, input/output devices, antennas, and the like, as required to perform its function.

The display can be a device display, a local display, or a remote display, operable to display an ICE message received from the processor. The ICE message includes emergency contact information which can be used to assist the patient under the emergency condition.

Figure 3:
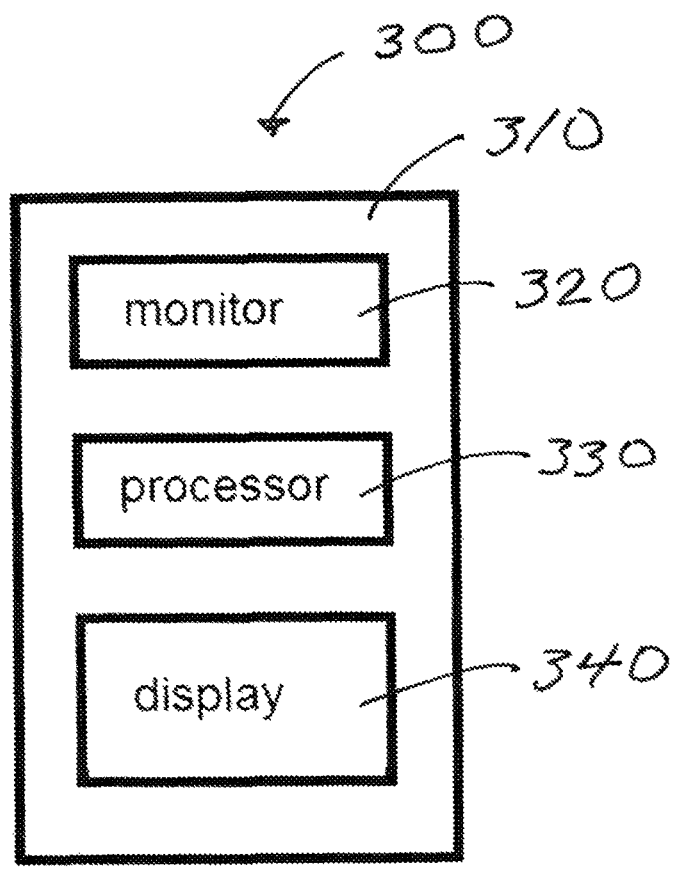
FIG. 3 is a schematic diagram of one embodiment of a personal medical system made in accordance with the invention.

FIG. 3 is a schematic diagram of a personal medical system made in accordance with the invention. In this embodiment, the display is a device display and the personal medical device includes the device display. The personal medical device 310 (also being the personal medical system 300 in this embodiment) includes a monitor 320, a processor 330, and a device display 340. In one embodiment, the monitor 320 is enclosed or incorporated in the case containing the monitor 320 and the processor 330. The device display 340 can be any type of display desired for a particular application, such as an LED display, an OLED display, an LCD display, or the like.

Figure 4:
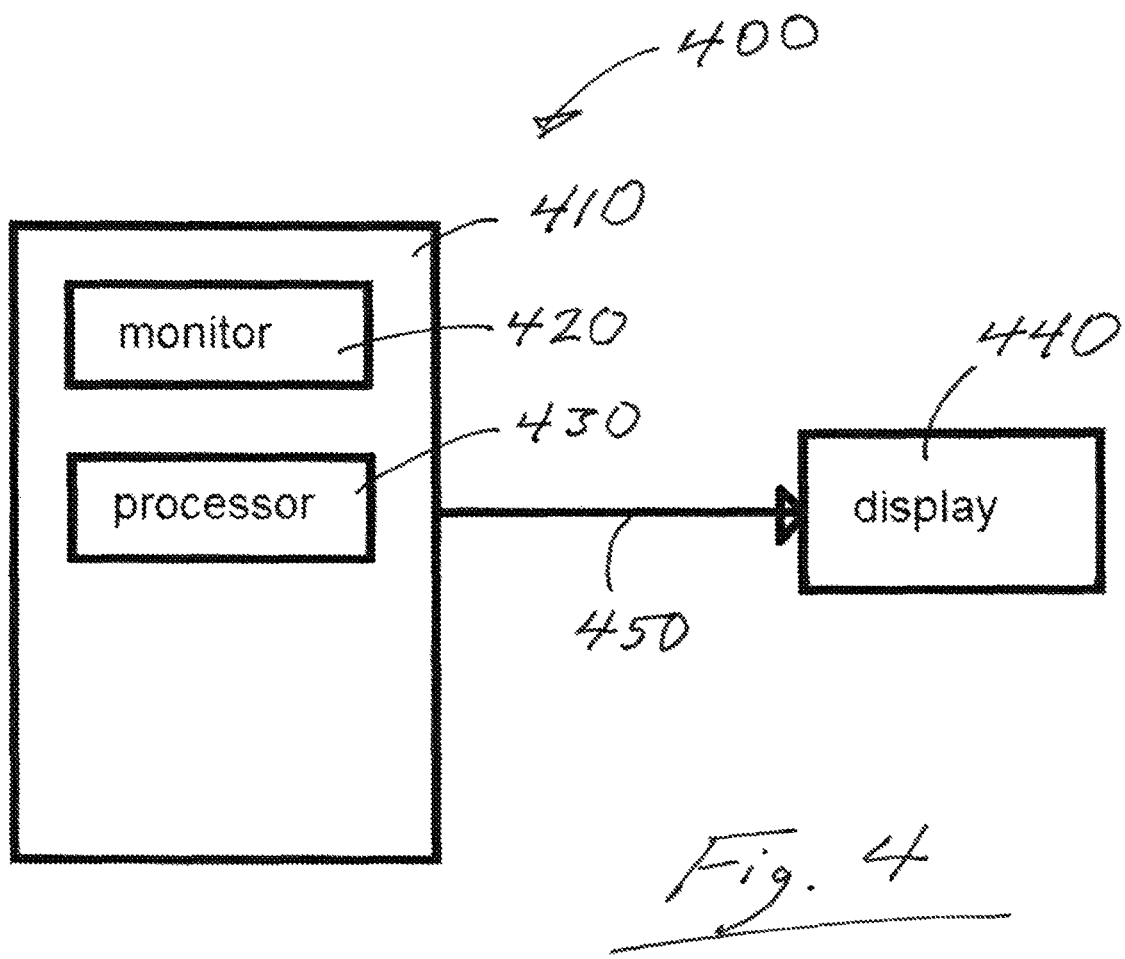
FIG. 4 is a schematic diagram of another embodiment of a personal medical system made in accordance with the invention.

FIG. 4 is a schematic diagram of another embodiment of a personal medical system made in accordance with the invention. In this embodiment, the display is a local display wirelessly connected to the personal medical device and the local display not being included in the personal medical device.

The personal medical system 400 includes a personal medical device 410 and a local display 440 wirelessly connected by local communication link 450 to the personal medical device 410, so that the local display 440 can receive and display an ICE message from the personal medical device 410. The personal medical device 410 includes a monitor 420 and a processor 430. Exemplary local communication links 450 include radio frequency connections, WiFi connections (such as Wi-Fi connections using 802.11b/g/n protocols), infrared (IR) connections, and Bluetooth connections, and the like having an unobstructed range of hundreds of feet at most. The local display 440 as defined herein as a display in the general vicinity of the personal medical device 410, and not being included in the personal medical device 410. Exemplary local displays 440 include relay device screens, cell phone screens, smart phone screens, dedicated monitors, computer monitors, computer tablet screens, game center displays, televisions, automobile displays, and the like, as long as the personal medical device 410 can reach the local display 440 over a local communication link 450. When the local display 440 is part of a smart phone, the ICE message can be received and processed with a smart phone app. In one embodiment, the local display 440 can also be a relay device to relay the ICE message to other devices or communication links. In one example, the local display 440 is a car navigation screen and the navigation system acts as a relay device, transmitting the ICE message to an automobile assistance service, such as OnStar or the like.

Figure 5:
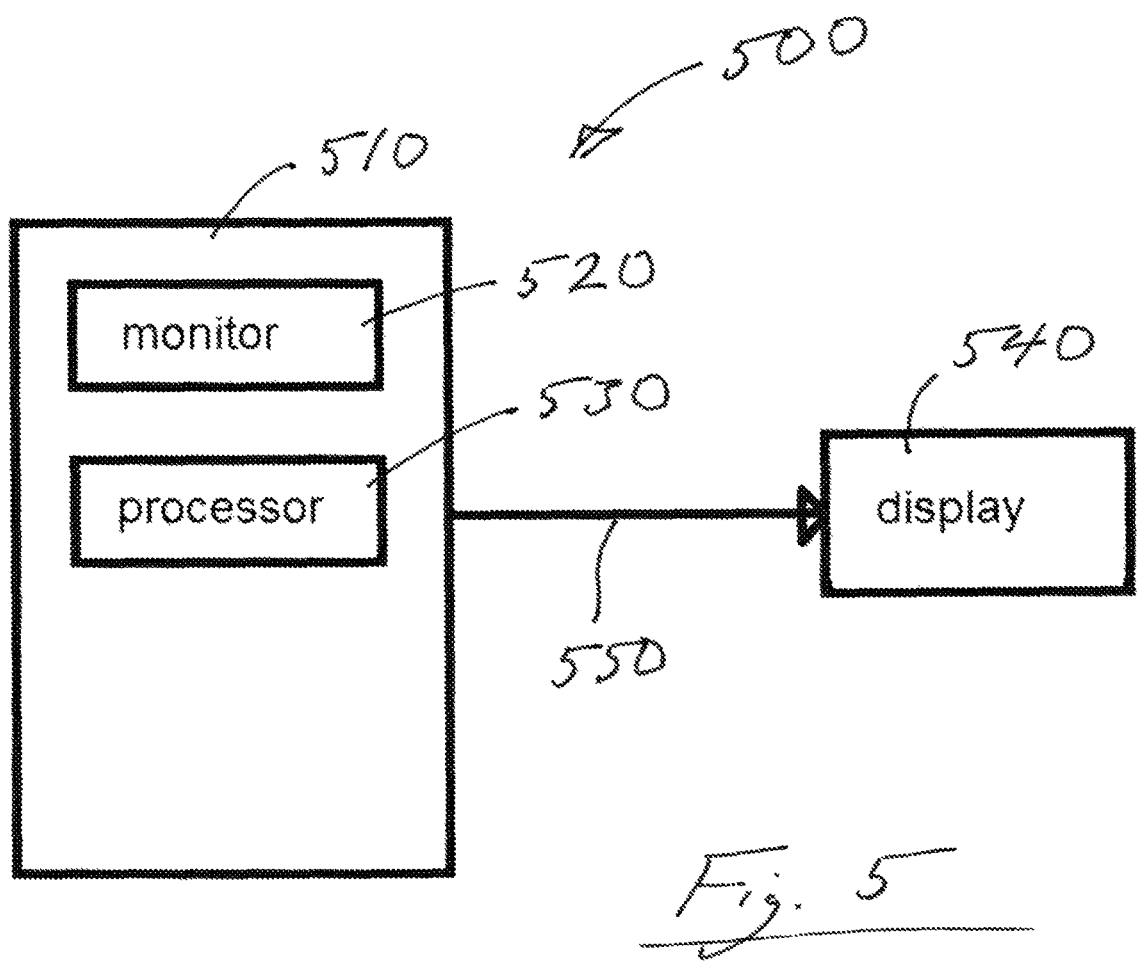
FIG. 5 is a schematic diagram of another embodiment of personal medical system made in accordance with the invention.

FIG. 5 is a schematic diagram of another embodiment of personal medical system made in accordance with the invention. In this embodiment, the display is a remote display operably connected to the personal medical device, the remote display not being included in the personal medical device.

The personal medical system 500 includes a personal medical device 510 and a remote display 540 operably connected by remote communication link 550 to the personal medical device 510, so that the remote display 540 can receive and display an ICE message from the personal medical device 510. The personal medical device 510 includes a monitor 520 and a processor 530. Exemplary remote communication links 550 include global computer networks, cellular networks, and the like having a range of miles, even a national or worldwide range. The remote display 540 as defined herein as a display accessible over a remote communication link 550, and not being included in the personal medical device 510. Exemplary remote displays 540 include dedicated display device screens, cell phone screens, smart phone screens, computer monitors, computer tablet screens, automobile displays, consumer device screens, Internet-enabled televisions screens, and the like, as long as the personal medical device 510 can reach the remote display 540 over a remote communication link 550. When the remote display 540 is part of a smart phone, the ICE message can be received and processed with a smart phone app. In one embodiment, the remote display 540 can also be a relay device to relay the ICE message to other devices or communication links. In one example, the remote display 540 is a car navigation screen in the navigation system acts as a relay device, transmitting the ICE message to an automobile assistance service, such as OnStar or the like.

Figure 6:
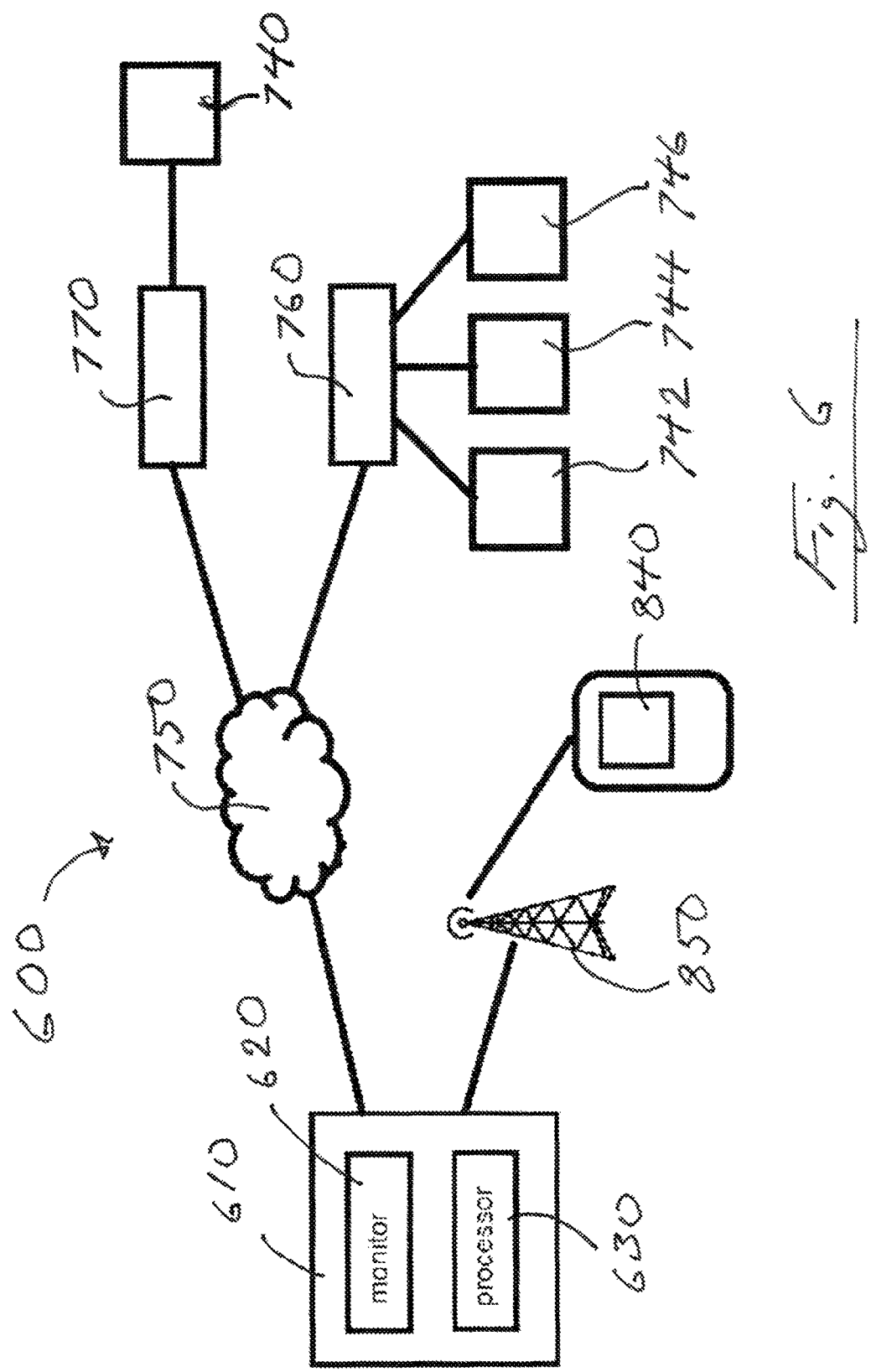
FIG. 6 is a schematic diagram of another embodiment of personal medical system made in accordance with the invention.

FIG. 6 is a schematic diagram of another embodiment of personal medical system made in accordance with the invention. In this example, the displays are remote displays.

The personal medical system 600 includes a personal medical device 610 and one or more remote displays operably connected by remote communication links to the personal medical device 610. The personal medical device 610 includes a monitor 620 and a processor 630. The remote displays can receive and display an ICE message from the personal medical device 610.

Remote display 840 is a cellular display operably connected to the personal medical device 610 over cellular network 850. In this example, the remote display 840 can be a cell phone screen, a smart phone screen, a computer tablet screen, or the screen on any other cellular enabled device.

Remote display 740 is a computer monitor operably connected to a computer 770, which is operably connected to the personal medical device 610 over global computer network 750, such as the Internet and the World Wide Web.

Remote displays 742, 744, 746 are remote displays operably connected to a relay device 760, which is operably connected to the personal medical device 610 over global computer network 750, such as the Internet and the World Wide Web. The relay device 760 is operable to relay the ICE message from the processor 630 of the personal medical device 610 to one or more of the remote displays 742, 744, 746. In one embodiment, the relay device 760 is operable to relay the ICE message to a number of the remote displays. In one embodiment, the relay device 760 is part of a home alarm system which transmits the ICE message to a central monitoring system when an emergency condition arises and a response is needed.

In one embodiment, the relay device 760 is operable to relay the ICE message to the nearest one of a number of remote displays. The personal medical device 610 can include a location detector operable to generate a device location message, which is included in the ICE message. The relay device 760 can decide which one of the remote displays 742, 744, 746 is nearest the personal medical device 610 and send the ICE message to the nearest one. In one embodiment, the patient can select one or more of the remote displays on which the ICE message is to appear by changing a list of remote displays stored in the personal medical device.

In one embodiment, the relay device 760 is operable to send an audible telephone message of the ICE message to a predetermined telephone number, Such as 911, a medical support service, the medical support service providing the personal medical device 610, a security service, or the like.

Figure 7:
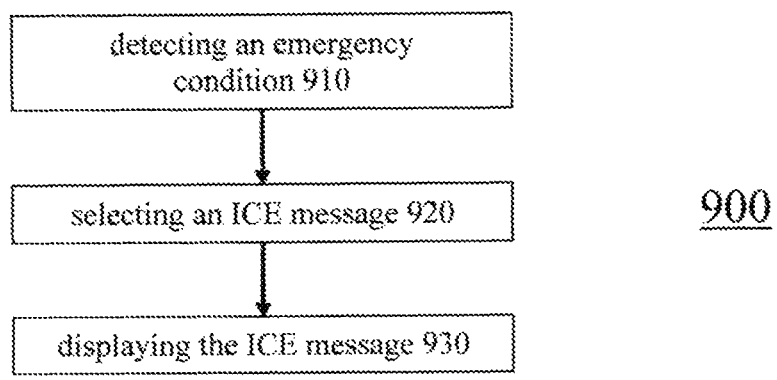
FIG. 7 is a flowchart for a method of emergency notification made in accordance with the invention.

FIG. 7 is a flowchart for a method of emergency notification made in accordance with the invention. The method can be used with a personal medical system as described in FIGS. 3-6 and an ICE message as described in FIG. 2. Referring to FIG. 7, the method 900 of emergency notification with a personal medical device attached to a patient includes detecting an emergency condition 910 at the personal medical device attached to the patient; selecting an ICE message 920 in response to the detected emergency condition; and displaying the ICE message 930. In one embodiment, the displaying 930 includes displaying the ICE message on a personal medical device attached to the patient. In one embodiment, the displaying 930 includes transmitting the ICE message wirelessly to a local display and displaying the ICE message on the local display. In one embodiment, the displaying 930 includes transmitting the ICE message over a global computer network to a remote display and displaying the ICE message on the remote display.

It is important to note that FIGS. 1-7 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:
1. A medical system for use with a patient, the system comprising:
  a personal medical device attached to the patient, the personal medical device comprising:
    a case attached to the patient;

a monitor contained in the case and operable to detect an emergency condition at the personal medical device; and a processor contained in the case and operably connected to the monitor and operable to select an ICE message in response to the emergency condition; and a display operably connected to the personal medical device and operable to display the ICE message, the ICE message including emergency contact information.

2. The system of claim 1 wherein the ICE message further includes a patient disease/condition identifier.

3. The system of claim 1 wherein the ICE message further includes a prospective cause indication determined by the processor in response to the emergency condition.

4. The system of claim 1 wherein the display is a device display, the personal medical device further comprising the device display contained in the case.

5. The system of claim 1 wherein the display is a local display wirelessly connected to the personal medical device, the local display not being included in the personal medical device.

6. The system of claim 5 wherein the local display is wirelessly connected to the personal medical device by a local communication link selected from the group consisting of a radio frequency connection, a WiFi connection, an infrared (IR) connection, and a Bluetooth connection.

7. The system of claim 5 wherein the local display is selected from the group consisting of a relay device screen, a cell phone screen, a smart phone screen, a dedicated monitor, a computer monitor, a computer tablet screen, a game center display, a television, and an automobile display.

8. The system of claim 1 wherein the display is a remote display operably connected to the personal medical device, the remote display not being included in the personal medical device.

9. The system of claim 8 wherein the remote display is operably connected to the personal medical device over a global computer network.

10. The system of claim 8 wherein the remote display is operably connected to the personal medical device over a cellular network.

11. The system of claim 8 wherein the remote display is selected from the group consisting of a dedicated display device screen, a cell phone screen, a smart phone screen, a computer monitor, a computer tablet screen, an automobile display, a consumer device screen, and an Internet-enabled televisions screens.

12. The system of claim 8 further comprising a relay device operable to relay the ICE message from the processor to the remote display.

13. The system of claim 12 wherein the relay device is operable to relay the ICE message to a plurality of remote displays.

14. The system of claim 13 wherein the personal medical device further comprises a location detector operable to generate a device location message, the ICE message further includes the device location message, and the relay device is operable to relay the ICE message to a nearest one of the plurality of remote displays.

15. The system of claim 12 wherein the relay device is operable to send an audible telephone message of the ICE message to a predetermined telephone number.

16. The system of claim 1 wherein the emergency condition is a medical emergency.

17. The system of claim 1 wherein the emergency condition is a failure to respond to a personal medical device alarm.

18. The system of claim 1 wherein the emergency condition is an equipment failure.

19. The system of claim 1 wherein the personal medical device further comprises a location detector operable to detect device position and the emergency condition is a failure to detect change in the device position.

20. A personal medical device attachable to a patient, the personal medical device comprising:

a case attached to the patient;

a monitor contained in the case and operable to detect an emergency condition at the patient;

a processor contained in the case and operably connected to the monitor and being operable to select an ICE message in response to the emergency condition, the ICE message including emergency contact information; and a display contained in the case and operably connected to the processor and being operable to present the ICE message.

* * * * *